United States Patent

Gilmutdinow et al.

Patent Number: 5,861,948
Date of Patent: Jan. 19, 1999

[54] ATOMIC ABSORPTION SPECTROPHOTOMETER

[75] Inventors: Albert H. Gilmutdinow; Konstantin J. Nagulin, both of g. Kasan, Russian Federation

[73] Assignee: Bodenseewerk Perkin-Elmer GmbH, Uberlingen, Germany

[21] Appl. No.: 976,327

[22] Filed: Nov. 21, 1997

Related U.S. Application Data

[62] Division of Ser. No. 492,061, filed as PCT/EP94/01022 Mar. 31, 1994, Pat. No. 5,742,388.

[30]  Foreign Application Priority Data

Apr. 2, 1993 [RU] Russian Federation .......... 930 17 152

[51] Int. Cl.⁶ ............................ G01N 21/74; G01N 21/31
[52] U.S. Cl. ............................................................. 356/312
[58] Field of Search ...................................... 356/311, 312

[56] References Cited

U.S. PATENT DOCUMENTS 4,204,770  5/1980  Tomoff .................................... 356/312
4,890,919  1/1990  Tsukada et al. ........................ 356/312

*Primary Examiner*—F. L. Evans
*Attorney, Agent, or Firm*—David Aker

[57]  ABSTRACT

The invention relates to optical instrment engineering. It is suggested that a linear solid state detector (photodiode array detector, charge coupled device, charge transfer device) that is positioned along the image of entrance slit of the monochrometer be used in an atomic absorption spectrophotometer. This will improve the analytical performance of an atomic absorption spectrophotometer—lower the detection limits, extend the range of concentrations to be measured, increase the reproducibility of measurements by taking into account the temporal and spatial non-uniformities of the analyte distribution over the atomizer volume and will simultaneously provide atomizer walls and of the platform temperatures.

9 Claims, 1 Drawing Sheet

ATOMIC ABSORPTION SPECTROPHOTOMETER

This is a divisional of application Ser. No. 08/492,061, filed as PCT/EP94/01022 Mar. 31, 1994, now U.S. Pat. No. 5,742,388.

The invention relates to optical instruments engineering and may be used when developing atomic absorption (AA) spectrophotometers with electrothermal atomizers.

BACKGROUND ART

At present, Atomic Absorption Spectrometry with electrothermal atomization is one of the most developed methods of determination of trace quantities of more than 60 elements in a variety of substances and materials. High sensitivity, selectivity and precision are characteristic of the method. An inherent feature of this method of analysis is non-stationarity of the analytical signal. All modern spectrophotometers record it with high temporal resolution; however, the signal recorded by a photomultiplier tube (PMT) at the instrument output is essentially an integrated characteristic of analytical volume as a whole and lacks spatial resolution. In the case of a uniform distribution of analyte atoms in the atomizer volume this causes no problems. However, as the imaging of analytical volume has shown, the atoms and molecules of the element to be determined may be distributed within the electrothermal atomizer extremely non-uniformly [(1)A. Kh. Gilmutdinov, Yu. A. Zakharov, V. P. Ivanov and A. V. Voloshin. Shadow Spectral Filming: A method of investigating Electrothermal Atomization. Part 1. Dynamics of Formation and Structure of the Absorption Layer of Thallium, Indium, Gallium and Alluminium Atoms. // Journ. Anal. Atom. Spectrometry, 1991, v. 6, p.505–519, (2) A. Kh. Gilmutdinov, Yu. A. Zakharov, V. P. Ivanov, A. V. Voloshin and K. Dittrich. Shadow Spectral Filming: A method of investigating Electrothermal Atomization. Part 2 Dynamics of Formation and Structure of the Absorption Layer of Tallium, Indium, Gallium and Alluminium Molecules. // Journ. Anal. Atom. Spectrometry, 1992, v. 6, p. 675–683.]. On the other hand, theoretical analysis [(3) A. Kh. Gilmutdinov, T. M. Abdullina, S. F. Gorbachev and V. L. Makarov. Formation of Analytical Signal in Electrothermal Atomic Absorption Spectrometry. Influence of temperature and concentration gradients. // Zhurn. Analit. Khimii, 1991, v. 46, p. 1480–1492.] shows that the analytical signal recorded at the spectrophotometer output depends not only on the number of absorbing atoms, but also on their distribution over the atomizer cross-section. This leads to two limitations in the existing detection systems. First, the relation between the absorbance recorded at the spectrophotometer output and the number of absorbing atoms proves to be ambiguous. Second, analytical curves appear to be largely curved in the region of high absorbances [3].

Thus, the use in an AA spectrophotometers of a detection system having no spatial resolution leads to narrowing of the range of concentrations to be measured due to curvature of analytical curves and to the increase of measurement error due to the ignored influence of absorption layers inhomogeneity. Therefore, to obtain a correct analytical signal, it is necessary to have a detection system ensuring not only sufficient temporal but also spatial resolution.

There exist a detection system of a AA spectrophotometer with a linear photodiode array detector [(4) Gary P. Moulton, Thomas C. O'Haver, James M. Harnly Continuum Source Atomic Absorption Spectrometry with a Pulsed Source a Photodiode Array Detector. // Journ. Anal. Atom. Spectrometry, 1989, v. 4, p. 673–674.]. In such a system the photodiode detector is positioned along the spectral instrument dispersion and besides the resonance line also records the radiation of adjacent lines.

However, such an arrangement of the photodiode array detector offers no possibility to use it for spatially resolved recording of the analytical signal. Therefore, such spectrophotometers have no spatial resolution and suffer from the drawbacks similar to the above shortcomings inherent in detection systems based on the use of photomultiplier tubes.

SUMMARY OF THE INVENTION

The object of the invention is to improve the analytical performance of an AA spectrophotometer, namely, lower its detection limits, extend the range of concentrations to be measured, increase the reproducibility of measurements by taking into account the temporal and spatial non-uniformities of the analyte distribution over the atomizer volume and simultaneous measuring of the atomizer walls and of the platform temperatures.

The above object is achieved by positioning a linear solid-state detector (potodiode array detector, charge coupled device, charge transfer device) in an atomic absorption spectrophotometer, consisting of a radiation source, optical illumination system and a monochromator, along the monochromator exit slit in the plane that is optically conjugated to the atomization zone.

DETAILED DESCRIPTION OF THE PREFERRED EMBODIMENT

Figure 1:
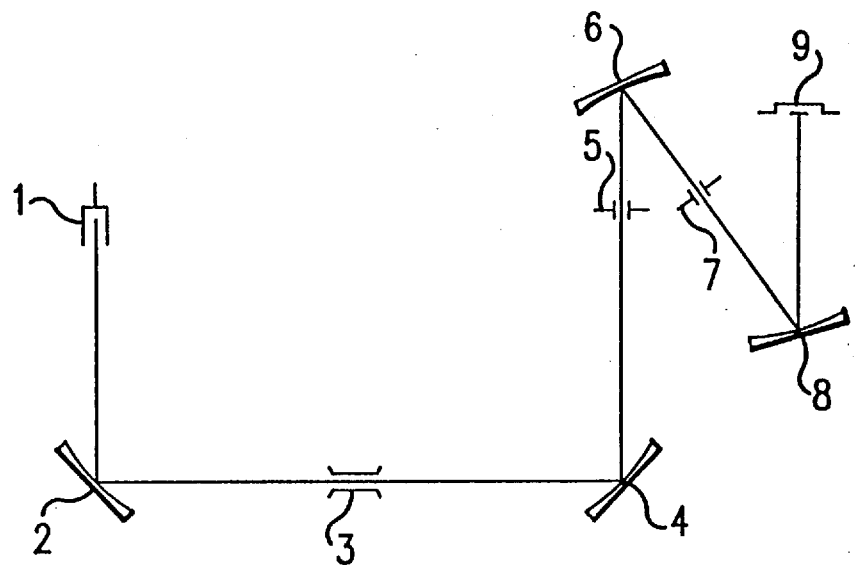
FIG. 1 is a schematic diagram of the optical system of a spectrophotometer according to the invention.
Figure 2:
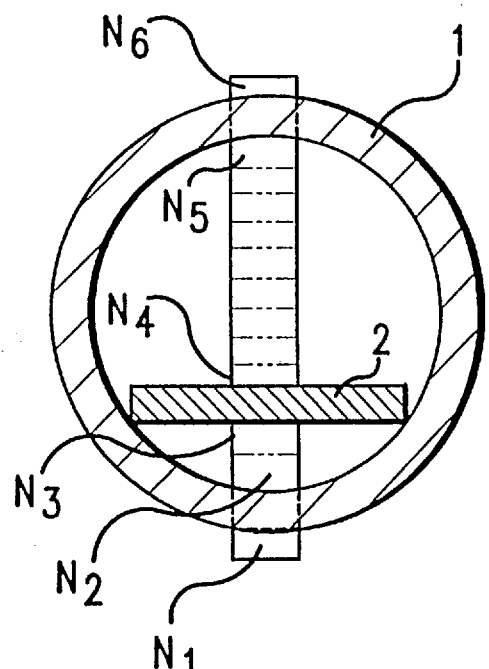
FIG. 2 is a cross-sectional view of the atomizer tube of FIG. 1 which illustrates the arrangement of detector pixels relative to the image elements of the atomizer volume.

The concept of the invention is illustrated by the AA spectrophotometer optical diagram (FIG. 1). The AA spectrophotometer comprises a linear spectrum radiation source 1, the illumination system consisting of optical elements 2 and 4, tube atomizer 3, monochromator consisting of entrance slit 5, grating 6 and exit slit 7, objective lens mirror 8 projecting the image of atomization zone onto the linear solid-state detector 9. FIG. 2 shows the arrangement of detector pixels relative to the image elements of the atomizer volume, where 1 is the cross-section of the atomizer tube, 2 is the platform, $N_1 \ldots N_6$ are ordinal numbers of detector array pixels.

The AA spectrophotometer with the solid-state detector operates in the following way. Optical radiation from the primary source 1 is directed by illumination system element 2 to the tube atomizer 3 where it passes through the analyte vapour and is partially absorbed in accordance with the vapour density distribution within the atomizer. The passed radiation is directed by illumination system element 4 to monochromator 5, 6, 7, the parameters of element 4 being selected so that the atomization plane is optically conjugated to monochromator entrance slit 5. Then objective lens 8 directs the radiation to linear photodiode array detector 9. Besides, the detector is spatially oriented in such a way that its array is parallel to the monochromator exit slit knives.

A certain area of the atomization zone corresponds to each detector pixel, i.e. a part of detector pixels measures the absorbance over a small cross-section area of the atomizer zone, whereas the other part measures the intensity of light radiation from the atomizer walls and from the platform. The electric signals received from each detector pixel prior to and during sample atomization are processed to determine the analyte distribution in the atomizer cross-section and absorbances over each elementary cross-section of atomization zone, as well as the temperature of the atomizer wall and of the platform during the whole atomization cycle. Then these elementary absorbances are summed up to obtain the absorbance of the analyte integrated over the furnace cross-section.

Part of the detector pixels records the radiation passed through the atomizer volume filled up with the absorbing atoms. The electric signals generated by these pixels is processed by means of the following equation:

$$A(t) = \sum_{N_2+1}^{N_3-1} lg \frac{I_0^j - I_d^j}{I^i - I_d^j} + \sum_{N_4+1}^{N_5-1} lg \frac{I_0^j - I_d^j}{I^i - I_d^j}$$

Here $A(t)$ is the absorbance integrated over the furnace cross-section at a moment of time t;

$I_O^i$ is the intensity of translucent emission from the prime source recorded by i-pixel prior to sample atomization;

$I_d^i$ is the intensity of dark signal from the detector i-pixel;

$I^i$ is the intensity of radiation from the prime source passed through the layer of absorbing atoms and recorded by the detector i-pixel;

$N_2$ is the number of the pixel to which the upper edge of the atomizer lower wall image corresponds;

$N_3$ is the number of the pixel to which the lower edge of the platform image corresponds;

$N_4$ is the number of the pixel to which the upper edge of the platform image corresponds;

$N_5$ is the number of pixel to which the lower edge of the atomizer upper wall image correpsonds;

The temperature of the graphite wall and of the platform is determined using the brightness method proceeding from the dependence of the heated graphite surface radiation intensity at a given wavelength on its temperature. To determine this dependence, calibration by the readings of a reference pyrometer is effected within the atomizer operating temperature range at each analytical wavelength. The intensity of radiation from a heated graphite surface is calculated from the following formula:

$$I_w(t) = \left[ \sum_{N_1}^{N_2} (I^i - I_d^i) + \sum_{N_5}^{N_6} (I^i - I_d^i) \right] / S(\lambda)$$

$$I_p(t) = \left[ \sum_{N_3}^{N_4} (I^i - I_d^i) \right] / S(\lambda)$$

where $I_w$ is the total intensity of radiation from the graphite tube walls recorded by linear solid-state detector; $I_p$ is the total intensity of radiation from the platform; $S(\lambda)$ is the function of absolute spectral response of the detector; $\lambda$ is the wavelength at which the measurement is taken; $N_1$ is the number of the pixel to which the lower edge of the atomizer lower wall image corresponds;

$N_6$ is the number of the pixel to which the upper edge of the atomizer upper wall image corresponds.

Then the temperature of the furnace walls and of the platform is determined by means of the formulae:

$$T_w = f_1(I_w, \lambda), \ T_p = f_2(I_p, \lambda)$$

Where $T_w$ is the temperature of the furnace wall;

$T_p$ is the platform temperature;

$f_1(I_w,\lambda)$ is the functional relation between the intensity of tube walls radiation and the walls temperature for the wavelength $\lambda$ obtained by calibration against a reference pyrometer;

$f_2(I_w,\lambda)$ is the functional relation between the intensity of the platform radiation and its temperature for the wavelength $\lambda$ obtained by calibration against a reference pyrometer.

As a result of the use of the present invention in atomic absorption spectrophotometers the following positive effect can be achieved. Measuring atomic absorbances with spatial resolution results in widening of the analytical curve linearity range and provides more accurate analytical results. Measurement of wall and platform temperatures using their radiation in the process of absorbance measurement allows one to obtain more complete information on the process of atomization and eliminates the necessity to use the atomizer temperature control unit. E.g. the additional information on the process of atomization can be utilised to correct the quantity values determined and/or can help to find out the optimal moment of quantity measurement.

We claim:

1. A method for determining the atomic absorption of a sample comprising:

introducing a sample containing analytes into an atomizer having a cross sectional area;

heating said atomizer to an operating temperature range where said sample vaporizes to form a sample vapor and said atomizer emits optical radiation;

passing a known optical radiation through said sample vapor;

measuring a value of known optical radiation transmitted through said sample vapor to obtain a measured value of said transmitted optical radiation;

measuring a value of optical radiation emitted from said atomizer to obtain a measured value of said emitted optical radiation; and obtaining an absorbance of a particular analyte integrated over a cross sectional area of said atomizer by manipulating said measured value of said transmitted optical radiation and said measured value of said emitted optical radiation.

2. A method according to claim 1 further comprising calibrating said atomizer by determining the intensity of emitted optical radiation from said atomizer at a series of specific wavelengths when said atomizer is heated over an operating temperature range.

3. A method according to claim 1 where said measured value of transmitted radiation and said measured value of emitted radiation are obtained by:

selecting a frequency or range of frequencies of said transmitted radiation and said emitted radiation;

further selecting within said frequency or said range of frequencies, portions of said transmitted radiation and said emitted radiation corresponding to locations on or within said atomizer;

projecting said portions of radiation onto a linear solid-state detector, said solid-state detector having an absolute spectral response, said detector including an array of (i) pixels for detecting optical radiation whereby said (i) pixels generate electrical signals corresponding to the intensity of optical radiation impinging on their surfaces; and measuring the electrical signals generated by said pixels.

4. A method according to claim 1 further comprising calibrating said atomizer by determining the intensity of emitted optical radiation from said atomizer at a series of specific wavelengths when said atomizer is heated over an operating temperature range, said atomizer comprising:

an upper wall and a lower wall, said upper and lower wall each having an upper edge and a lower edge; and a platform having an upper edge and a lower edge mounted in close proximity to said lower wall.

5. A method according to claim 4 where said measured value of transmitted radiation and said measured value of emitted radiation are obtained by:

selecting a frequency or range of frequencies of said transmitted radiation and said emitted radiation;

further selecting within said frequency or said range of frequencies, portions of said transmitted radiation and said emitted radiation corresponding to locations on or within said atomizer;

projecting said portions of radiation onto a linear solid-state detector said solid-state detector having an absolute spectral response, said detector including an array of (i) pixels for detecting optical radiation whereby said (i) pixels generate electrical signals corresponding to the intensity of optical radiation impinging on their surfaces; and measuring the electrical signals generated by said pixels.

6. A method according to claim 5 wherein:

at least one pixel is arranged so as to receive said emitted radiation from said upper edge of said upper wall of said atomizer;

at least one pixel is arranged so as to receive said emitted radiation from said lower edge of said upper wall of said atomizer;

at least one pixel is arranged so as to receive said emitted radiation from said upper edge of said lower wall of said atomizer;

at least one pixel is arranged so as to receive said emitted radiation from said lower edge of said lower wall of said atomizer;

at least one pixel is arranged so as to receive said emitted radiation from said upper edge of said platform; and at least one pixel is arranged so as to receive said emitted radiation from said lower edge of said platform.

7. A method according to claim 5 wherein: said (i) pixels generate a dark signal when there is no optical radiation impinging on their surfaces; and said measured value of transmitted radiation and said measured value of emitted radiation are manipulated to obtain the absorption of a particular analyte integrated over the cross sectional area of said atomizer by utilizing the equations:

$$A(t) = \sum_{N_2+1}^{N_3-1} lg \frac{I_0^i - I_d^i}{I^i - I_d^i} + \sum_{N_4+1}^{N_5-1} lg \frac{I_0^i - I_d^i}{I^i - I_d^i}$$

Where A(t) is the absorbance integrated over the cross-section of said atomizer at a moment of time t;

$I_o^i$ is the intensity of known optical radiation recorded by said (i) pixel prior to sample atomization;

$I_d^i$ is the intensity of dark signal from said detector (i) pixel;

$I^i$ is the intensity of known optical radiation transmitted through said sample vapor by said detector (i) pixel;

$N_2$ is the number of said at least one pixel to which the upper edge of the atomizer lower wall image corresponds;

$N_3$ is the number of said at least one pixel to which the lower edge of the platform image corresponds;

$N_4$ is the number of said at least one pixel to which the upper edge of the platform image corresponds;

$N_5$ is the number of said at least one pixel to which the lower edge of the atomizer upper wall image corresponds;

and $$I_w(t) = \left[ \sum_{N_1}^{N_2} (I^i - I_d^i) + \sum_{N_5}^{N_6} (I^i - I_d^i) \right] / S(\lambda)$$

$$I_p(t) = \left[ \sum_{N_3}^{N_4} (I^i - I_d^i) \right] / S(\lambda)$$

Where $I_w$ is the total intensity of radiation from said atomizer walls at a moment in time (T);

$I_p$ is the total intensity of radiation from said platform;

$S(\lambda)$ is the function of absolute spectral response of said linear solid-state detector;

$\lambda$ is the wavelength at which $I^i$ and $I_d^i$ are measured;

$N_1$ is the number of said at least one pixel to which the lower edge of the atomizer lower wall image corresponds;

$N_6$ is the number of said at least one pixel to which the upper edge of the atomizer upper wall image corresponds; and $$T_w = f_1(I_w, \lambda); \; T_p = f_2(I_p, \lambda)$$

Where $T_w$ is the temperature of the furnace wall;

$T_p$ is the platform temperature;

$F_1(I_w, \lambda)$ is the functional relation between the intensity of radiation from said atomizer upper and lower walls and the temperature of said atomizer upper and lower walls for the wavelength $\lambda$ obtained during calibration;

$F_2(I_w, \lambda)$ is the functional relation between the intensity of said platform radiation and its temperature for the wavelength $\lambda$ obtained during calibration.

8. A method according to claim 6 wherein: said (i) pixels generate a dark signal when there is no optical radiation impinging on their surfaces; and said measured value of transmitted radiation and said measured value of emitted radiation are manipulated to obtain the absorption of a particular analyte integrated over the cross sectional area of said atomizer by utilizing the equations:

$$A(t) = \sum_{N_2+1}^{N_3-1} lg \frac{I_0^i - I_d^i}{I^i - I_d^i} + \sum_{N_4+1}^{N_5-1} lg \frac{I_0^i - I_d^i}{I^i - I_d^i}$$

Where A(t) is the absorbance integrated over the cross-section of said atomizer at a moment of time t;

$I_o^i$ is the intensity of known optical radiation recorded by said (i) pixel prior to sample atomization;

$I_d^i$ is the intensity of dark signal from said detector (i) pixel;

$I_i$ is the intensity of known optical radiation transmitted through said sample vapor by said detector (i) pixel;

$N_2$ is the number of said at least one pixel to which the upper edge of the atomizer lower wall image corresponds;

$N_3$ is the number of said at least one pixel to which the lower edge of the platform image corresponds;

$N_4$ is the number of said at least one pixel to which the upper edge of the platform image corresponds;

$N_5$ is the number of said at least one pixel to which the lower edge of the atomizer upper wall image corresponds; and $$I_w(t) = \left[ \sum_{N_1}^{N_2} (I^i - I_d^i) + \sum_{N_5}^{N_6} (I^i - I_d^i) \right] / S(\lambda)$$

$$I_p(t) = \left[ \sum_{N_3}^{N_4} (I^i - I_d^i) \right] / S(\lambda)$$

Where $I_w$ is the total intensity of radiation from said atomizer walls at a moment in time (t);

$I_p$ is the total intensity of radiation from said platform;

$S(\lambda)$ is the function of absolute spectral response of said linear solid-state detector;

$\lambda$ is the wavelength at which $I^i$ and $I^i_d$ are measured;

$N_1$ is the number of said at least one pixel to which the lower edge of the atomizer lower wall image corresponds;

$N_6$ is the number of said at least one pixel to which the upper edge of the atomizer upper wall image corresponds; and $$T_w = f_1(I_w, \lambda), \quad T_p = f_2(I_p, \lambda)$$

Where $T_w$ is the temperature of the furnace wall;

$T_p$ is the platform temperature;

$F_1(I_w, \lambda)$ is the functional relation between the intensity of radiation from said atomizer upper and lower walls and the temperature of said atomizer upper and lower walls for the wavelength $\lambda$ obtained during calibration;

$F_2(I_w, \lambda)$ is the functional relation between the intensity of said platform radiation and its temperature for the wavelength $\lambda$ obtained during calibration.

9. A method according to claim 4 wherein:

at least one pixel is arranged so as to receive said emitted radiation from said upper edge of said upper wall of said atomizer;

at least one pixel is arranged so as to receive said emitted radiation from said lower edge of said upper wall of said atomizer;

at least one pixel is arranged so as to receive said emitted radiation from said upper edge of said lower wall of said atomizer;

at least one pixel is arranged so as to receive said emitted radiation from said lower edge of said lower wall of said atomizer;

at least one pixel is arranged so as to receive said emitted radiation from said upper edge of said platform; and at least one pixel is arranged so as to receive said emitted radiation from said lower edge of said platform.

* * * * *